United States Patent [19]

Vasquez et al.

[11] Patent Number: 4,851,209

[45] Date of Patent: Jul. 25, 1989

[54] DIAGNOSTIC PROCEDURES USING RADIO LABELED SUCRALFATE AND DERIVATIVES OR PRECURSORS THEREOF

[75] Inventors: Tony E. Vasquez, Cardiff; Robert L. Bridges, Corona; Philip Braunstein; Anne-Line Jansholt, both of Irvine, all of Calif.

[73] Assignee: The Regents of the University of California, Calif.

[21] Appl. No.: 734,708

[22] Filed: May 16, 1985

Related U.S. Application Data

[63] Continuation-in-part of Ser. No. 483,757, Apr. 11, 1983, abandoned, which is a continuation-in-part of Ser. No. 441,211, Nov. 12, 1982, abandoned.

[51] Int. Cl.$^4$ .................. A61K 49/02; A61K 49/00
[52] U.S. Cl. .................. 424/1.1; 534/14; 424/9
[58] Field of Search .................. 424/1.1, 9; 534/14

[56] References Cited

U.S. PATENT DOCUMENTS

| | | | |
|---|---|---|---|
| 3,432,489 | 3/1969 | Nitta et al. | 536/118 |
| 3,852,413 | 12/1974 | Cammarata | 424/1.1 |
| 4,243,652 | 1/1981 | Francis | 424/1.1 |
| 4,385,046 | 5/1983 | Milbrath et al. | 424/1.1 |
| 4,581,221 | 4/1986 | Kuperus | 424/1.1 |

OTHER PUBLICATIONS

Nagashima et al., Arzneimittel Forschung, 30(1), 80–91, (1980).
Wu et al., Nuclear Medicine and Biology Advances, 3, 2961–2963.
Braunstein et al., Abstract from American Gastroenterological Assn., May 23, 1983, "Detection of Peptic Ulcer Disease by Nuclear Scintigraphy Using an Ulcer Avid Acent".
P. Braunstein, 1983 Abstract, Soc. of Nuclear Medicine, Jun. 7–8, 1983, "Tagged Ulcer-Avid Material Imaging (Tumi): A Potent New Method for the Evaluation of Peptic Ulcer Disease".
Journal of Clinical Gastroenterology, Supp. 2, 1981, "Sucralfate Mechanisms of Action".
Arzneim Forsch/Drug Res. 30(I), Nr.1, 1980, N. Hirano, "Sucralfate".
Arzneim-Forsch/Drug Res. 30 (I), 1979, Several Articles, pp. 73–80.
Vasquez, T., *Radiology* 148: 227–231, Jul. 1983, "Work in Progress, Gastro-Intestinal Ulcerations: Detection Using a Technetium-99 m-Labeled Ulcer-Avid Agent".
Vasquez, T., *Jour. Nuc. Med.*, 30: No. 2–3, 1986, "Radionuclide Imaging Using Technetium-99 m Labeled Sucralfate and Potassium Sucrose Sulfate to Detect Gastric and Duodenal Ulcers".
Vasquez, T., From FDA IND Application, 7-27-84, "Detection of Upper Gastro-Intestinal Tract Mucosal Injury with a Radiolabeled Ulcer-Avid Agent".
Vasquez, Tony, Abstract, 9/3/82, "Nuclear Imaging of Gastrointestinal (G.I.) Ulceration: A New Non Invasive Procedure Using an Ulcer Avid Agent".
Vasquez, T., *8–Radiation*, vol. 99:49703q, p. 49704, "Work in progress. Gastrointestinal Ulcerations: Detecting Using a Technetium-99-m-Labeled Ulcer-Avid agent".
Wu, R. K., *Nuc. Med. and Bio. Advances*, Radiation, Aug., 1982, "Radiation Dose Calculations for Orally Administered Radio-Pharmaceuticals in Upper Gastrointestinal Disease".

*Primary Examiner*—John F. Terapane
*Assistant Examiner*—J. E. Thomas
*Attorney, Agent, or Firm*—Ciotti & Murashige, Irell & Manella

[57] ABSTRACT

A novel diagnostic procedure for the in vivo clinical evaluation of gastrointestinal ulcer disease and other diseases associated with loss of mucosal integrity in humans which comprises the oral administration of an effective amount of radio-labeled sucralfate or derivative or precusor thereof or a water soluble, physiologically compatible radiolabeled salt of sucrose suflate to the human host, followed by scintigraphic imaging of the gastrointestinal area of interest with scintigraphic imaging equipment.

A novel radiopharmaceutical composition comprising an aqueous solution or suspension containing an amount of a radio-labeled sucralfate or derivative or precursor thereof or a water soluble, physiologically compatible radiolabeled salt of sucrose sulfate for in vivo scintigraphic imaging of the gastrointestinal or other muscosal areas in humans.

10 Claims, No Drawings

DIAGNOSTIC PROCEDURES USING RADIO LABELED SUCRALFATE AND DERIVATIVES OR PRECURSORS THEREOF

This is a continuation-in-part of U.S. patent application Ser. No. 483,757, now abandoned, filed Apr. 11, 1983, which was a continuation-in-part of U.S. patent application Ser. No. 441,211, filed Nov. 12, 1982, now abandoned.

BACKGROUND OF THE INVENTION

A new Food and Drug Administration approved drug, Sucralfate, for the short-term treatment of upper gastrointestinal ulcers, has been proven to bind selectively to ulcerated areas in the upper G. I. tract. Several clinical trials have shown the safety and efficacy of Sucralfate in healing duodenal ulcers.

Radiologic studies are preferred by many as the first diagnostic procedure when intentinal disease is suspected. They are reasonably accurate in detecting ulcer disease in most instances. Radiologic studies are more widely available are are noninvasive, safer and less expensive then endoscopy, *Applied Radiology*, May/June 1982, pp. 20 and 120.

It is known that sucralfate binds to duodenal and gastric ulcers and to gastric erosions produced by ethanol and anti-inflammatory drugs. The affinity of sucralfate for defective mucosa is explained by the drug's viscous adhesivesness and the formation of polyvalent bridges between the negatively charged sucralfate polyanions and positively charged proteins present in high concentrations in mucosal lesions. Sucralfate also buffers acid, inhibits the action of pepsin, and adsorbs bile salts. These properties of sucralfate enable the drug to act as an effective barrier to the penetration of acid, pepsin, and bile salts. Sucralfate also binds to uninjured mucosa to a much lesser extent and is believed to exert a similar "barrier" effect on regenerated and normal mucosa. Other possible mechanisms for sucralfate's antiulcer effect include depletion of acid, pepsin, bile salts from the gastric secretion. Animal data show that the action of sucralfate is sustained because of its viscous adhesiveness, slow reaction with acid, and high affinity for areas with defectice mucosa, J. Clin. Gastroenterol 2 (supp 2):117–127, 1981.

Studies involving $^{14}C$-labeled sucralfate in rats using histoautoradiographic methods have also been reported, Duodenal Ulcer Gatric Ulcer, Sucralfate, a New Therapeutic Concept, edited by Wolfgang F. Caspary, Hanau, West Germany, published by Urban and Schwarzenberg, Munchen-Wien-Baltimore, 1981, pp 19–21. However, $^{14}C$-labeled sucralfate is unsuited for in vivo imaging in humans.

We have developed a simple method for labeling Sucralfate with Tc-99m and other radio labels. The resulting suspension is easily administered orally and imaging may be carried out with standard scintigraphic equipment. Preliminary animal and human studies show that the agent is stable in vivo and has clinical utility for the evaluation of gastrointestinal ulcer disease along with other diseases that are associated with loss of mucosal integrity.

The method is simple, should have ready patient acceptability and be associated with low radiation doses. It is believed that the present invention presents a significant advance in the art.

SUMMARY OF THE INVENTION

Briefly, the present invention comprises a novel diagnostic procedure for the in vivo clinical evaluation of gastrointestinal ulcer disease and other diseases associated with loss of muscosal integrity in humans which comprises the oral administration of an effective amount of radiolabeled sucralfate or derivative or precursor thereof or a water soluble, physiologically compatible radiolabeled salt of sucrose sulfate to the human host, followed by scintigraphic imaging of the gastrointestinal areas of interest with scintigraphic imaging equipment.

The invention further comprises radiolabeled sucralfate or derivative or precursors thereof or a water soluble, physiologically compatible radiolabeled salt of sucrose sulfate wherein the radiolabel is one suitable for in vivo imaging in humans.

The invention still further comprises a novel radiopharmaceutical composition of an aqueous suspension or solution containing an amount of a radiolabeled sucralfate or derivative or precursors thereof or a water soluble, physiologically compatible radiolabeled salt of sucrose sulfate effective for in vivo scintigraphic imaging of the gastrointestinal tract and other muscosal areas in humans.

It is an object of this invention to provide a new radioimaging technique for the in vivo detection of ulcers and related and associated diseases of the mucosa of the gastrointestinal tract including ulcerative colitis and Crohn's disease.

It is also an object to provide an improved diagnostic technique useful for the detection of certain diseases in humans.

A further object of this invention is to employ radiolabeled sucralfate or derivatives or precursors thereof or a water soluble, physiologically compatible radiolabeled salt of sucrose sulfate in a novel diagnostic procedure.

These and other objects and advantages of our invention will be apparent from the more detailed discussion which follows.

DESCRIPTION OF THE PREFERRED EMBODIMENTS

Technetium-99m labeled Sucralfate combines a short lived radioisotope which is most suitable for diagnostic imaging with a new oral medication which selectively binds to ulcers in the stomach and upper small bowel. This provides a safe, noninvasive and benign way to detect, localize and access for the presence and the activity of ulcer disease in the upper GI tract, both for initial diagnosis and follow-up evaluation.

The utility provided by our invention would replace or significantly decrease the need for the alternative methods of making a diagnosis which are relatively costly, less than adequately sensitive, often uncomfortable, and occasionally associated with significant risks.

There are no published data describing the use of radiotracer labeled Sucralfate or any other ulcer avid agent for the diagnosis of gastrointestinal ulcer disease.

The following Example is presented solely to illustrate the invention and should not be regarded as limiting in any way.

EXAMPLE I 1. 1–2 crushed sucralfate tablets (1 gram per tablet were suspended in HCl at a pH of about 1 to 2.

2. 2–3 millicuries Technetium-99m labeled Human Serum Albumin were combined with the Sucralfate in the presence of stannous tartrate.

3. The resultant compound was washed with deionized water.

4. The drug was then administered orally in the form of a suspension of the product in water.

5. The gastrointestinal area of the patient was then imaged with a gamma camera.

Other modifications include tagging Sucralfate with other Technetium-99m compounds or other radioisotope labels useful for imaging. For example, $I^{131}$ can be used. Positron emitters can be used in lieu of gamma emitters. It is also intended to use other human or non-human proteins or protein derivatives in place of human serum albumin to aid in radio labeling. The sucralfate can be replaced by derivatives thereof, preferably basic aluminum salts of a sulfated disccaride, per se, a known class of compounds. The sucralfate can also be replaced by sucralfate precursors, for example, the sucrose moiety of sucralfate or related compounds, also a known class of chemical compounds.

The sucralfate or derivative or precursor thereof is preferably labeled under acidic conditions with radiolabeled human serum albumin. However, amino acids, bovine albumin and other lower molecular weight proteins can also be used. The acidic conditions can be provided by HCl or any other mild acid.

The stannous tartrate in the Example acts as a reducing agent and other reducing agent will be useful for this purpose.

We anticipate based on our animal studies, that studies with this agent will be significantly more sensitive for the detection and localization, etc. of upper gastrointestinal ulcer disease than either of the only other two modalities available for this purpose, i.e., upper gastrointestinal barium x-ray series or endoscopy. We have been able to clearly identify ulcers in rabbits as small as 1 mm in size. These are most unlikely to be detected by the currently used methods. Furthermore, it should be associated with only a possible minimal risk from radiation, albeit lower in general than with upper GI series. It will also likely involve the patient only in minimal degree of discomfort and psychological stress. Upper GI series and endoscopy are unpleasant, occasionally are associated with significant risk and/or require ability for agile cooperation on the part of the patients.

EXAMPLE II

Initial studies in humans were conducted in three patients having confirmed ulcer disease. A one gram sucralfate tablet was first acidified and then labeled with 2 to 3 millicuries Technetium -99m labeled albumin and made into an aqueous suspension. A small amount of an inert binder was also present. The acid was washed away leaving a slurry of fine particles which were then mixed with about 5 cc of water and administered orally by swallowing. Imaging showed clearly that the labeled drug adhered selectively to the ulcerated portion of the mucosa. These areas were apparent.

EXAMPLE III

We have tested Tc-99m labeled potassium sucrose sulfate on two supine human volunteers. The tagged material was stable in a solution comprising one gram per 10 cc of normal saline. The solution was given orally as a 10 cc dose. The material had a fast half-time clearance from the stomach (i.e. half of the material has left the stomach in a certain time T1/2). The T1/2 of the labeled potassium sucrose sulfate is r22 minutes from the stomach vs. r90 minutes for radiolabeled sucralfate. The value of Tc-99m potassium sucrose sulfate vs. Tc99m sucralfate is that the residual of the former is less than that of Tc-99m sucralfate. Thus, at 90 minutes there is only a minimum of labeled potassium sucrose sulfate left in the stomach to confuse a physician looking for hot spots on a gamma camera (ulcers) as compared to 50% of Tc-99m sucralfate at the same time. A good analogy would be the stars at night vs. the stars during the day. The stars are there in both instances. However, the sky is so bright during the day that starlight is simply lost in the background. By utilizing radiolabeled potassium sucrose sulfate the background is reduced to bring out the ulcers. Radiolabeled potassium sucrose sulfate offers a substantial improvement as a radio-pharmaceutical over the use of radiolabeled sucralfate. The potassium salt used for imaging ulcers in Example III can be replaced by other cations compatible in the human body including alkali metal and alkaline earth metal cations such as sodium and calcium.

It is estimated that 10% of the U.S. population has upper gastrointestinal ulcer diseae. Most of these patients will undergo either one or both of the presently available studies, i.e. endoscopy or upper gastrointestinal x-rays repeatedly. In addition, a large number of patients who do not have ulcer disease undergo these examinations in order to rule such disease out.

The radiolabel is present in an effective amount per dose which is usually on the order of 1 or 2 or more up to 10 millicuries or even more.

Having fully described the invention, it is intended that it be limited only the lawful scope of the appended claims.

We claim:

1. A method for clinical evaluation of conditions associated with loss of mucosal integrity in humans which comprises:
    administering orally to a subject in need of such evaluation an effective amount of a polysulfated disaccharide salt labeled by association with a carrier containing a radioisotope detectable by scintigraphic imaging.
    followed by scintigraphic imaging of the gastrointestinal area.

2. The method of claim 1 wherein the salt is an aluminum salt.

3. The method of claim 2 wherein the disaccharide salt is sucralfate.

4. The method of claim 1 wherein the radioisotope is technetium-99.

5. The method of claim 1 wherein the carrier is human serum albumin.

6. A composition useful for evaluation by radioimaging of conditions associated with loss of mucosal integrity, which composition comprises an effective amount of polysulfated disaccharide salt associated with a carrier containing a radioisotope detectable by scintigraphy.

7. The composition of claim 6 wherein the salt is an aluminum salt.

8. The composition of claim 7 wherein the disaccharide salt is sucralfate.

9. The composition of claim 6 wherein the radioisotope is technetium-99.

10. The composition of claim 6 wherein the carrier is human serum albumin.

* * * * *